US00PP18502P2

(12) United States Plant Patent
Korlipara

(10) Patent No.: US PP18,502 P2
(45) Date of Patent: Feb. 19, 2008

(54) ***COREOPSIS* PLANT NAMED 'RP1'**

(50) Latin Name: ***Coreopsis* hybrid**
Varietal Denomination: RP1

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 7 days.

(21) Appl. No.: 11/592,654

(22) Filed: Nov. 3, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP15,455 P3 * 12/2004 Faria ..... Plt./263

* cited by examiner

*Primary Examiner*—Wendy Haas
(74) *Attorney, Agent, or Firm*—Klarquist Sparkman, LLP

(57) ABSTRACT

A new and distinct *Coreopsis* plant named 'RP #1', characterized by numerous, small, free flowering, copper-colored daisy-like flowers, a pincushion habit and excellent vigor.

1 Drawing Sheet

Figure 1:
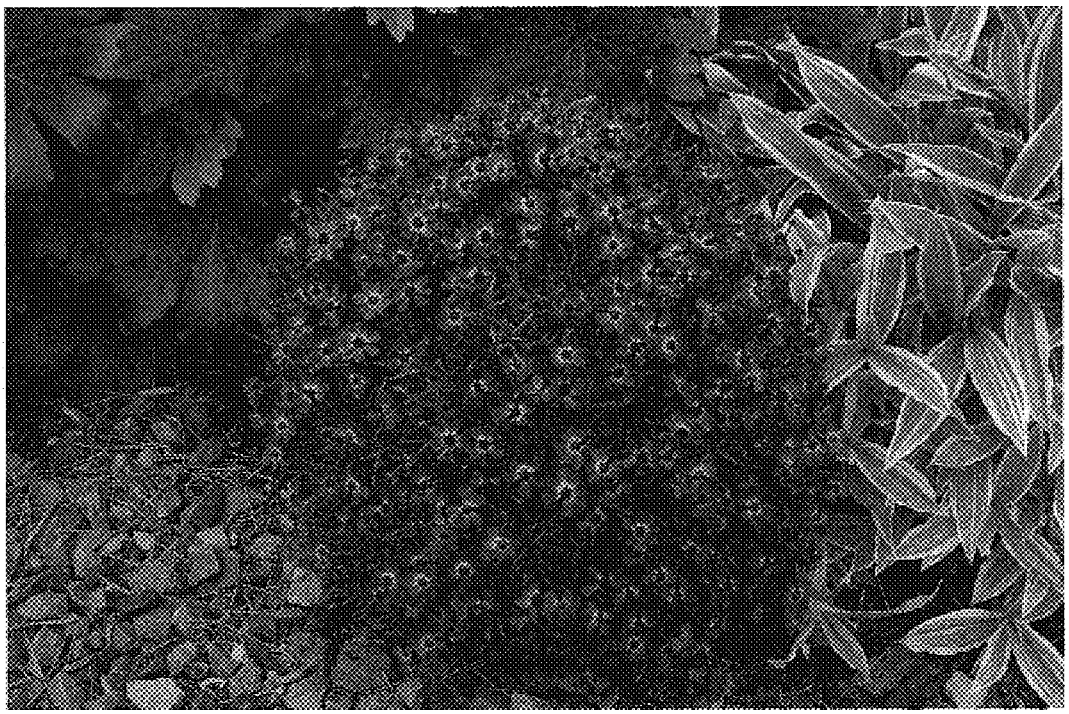

Botanical designation: *Coreopsis* hybrid (of unknown origin).
Variety denomination: 'RP #1'.

BACKGROUND OF THE INVENTION

The present invention relates to a new and distinct plant of *Coreopsis* and given the cultivar name 'RP #1'. *Coreopsis* is in the family Asteraceae. This new cultivar originated as a whole plant tissue culture mutation from *Coreopsis* 'Rum Punch' (U.S. Plant patent application Ser. No. 11/488,815). 'RP #1' stood out with its extremely tight and compact habit.

SUMMARY OF THE INVENTION

The following traits have been repeatedly observed and are determined to be the unique characteristics of 'RP #1'. These characteristics in combination distinguish 'RP #1' as a new and distinct cultivar:

1. Numerous, small copper-colored daisy-like flowers.
2. Low pincushion habit.
3. Very free flowering and blooms continuously all summer.
4. Excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

FIG. 1 shows a one year old *Coreopsis* 'RP #1' growing in the ground in the garden in full sun in August in Canby, Oreg.

DETAILED PLANT DESCRIPTION

The following is a detailed description of the new *Coreopsis* cultivar based on observations of a one-year-old specimen grown in the ground in full sun under typical outdoor conditions in the trial fields in August in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Type.*—Herbaceous perennial, grown as an annual.
- *Hardiness.*—USDA Zone 9-10.
- *Size.*—40 cm wide and 20 cm tall to top of flowers.
- *Form.*—Pincushion (very low mound with freely branching stems).
- *Vigor.*—Excellent.
- *Roots.*—Fibrous, freely branching, fine, and Yellow White 158A; roots develop easily from stem cuttings.

Stem:
- *Type.*—Ascending.
- *Size.*—Grows with branches to 20 cm tall and 3 mm wide.
- *Internode length.*—Grows to 2 cm, most 1 cm.
- *Surface.*—Glabrous.
- *Color.*—Green 137B with the base being Grey Brown 199A.

Leaf:
- *Type.*—Simple.
- *Shape.*—Linear.
- *Arrangement.*—Opposite.
- *Size.*—Grows to 2.5 mm long and 1.2 mm wide.
- *Margins.*—Entire except at the base where sparsely pubescent.
- *Apex.*—Acute.
- *Base.*—Cuneate, clasping.
- *Surface texture.*—Glabrous on top and bottom side.
- *Venation.*—Pinnate.

*Color.*—Top side — Green 147A. Bottom — Green 147A.

Immature inflorescence: Globular, 4 mm wide and 3.5 mm deep, Greyed Purple 187A, glabrous.

Inflorescence:

*Type.*—Long stalked terminal heads of daisy type flowers.

*Peduncle.*—Grows to 5.5 cm long and 0.6 mm wide, glabrous, Green 137A.

*Size.*—2.5 cm wide and 7 mm deep.

*Ray florets.*—8 in number, no pistil or stamen, obovate, the tip three lobed with the terminal lobe the longest, margins entire, base cuneate, 13 mm long and 5 mm wide, glabrous on both surfaces, 3 mm claw at base, laminae with linear appendage on side or opposite and upright, 6 mm long. Color: Ray flower, topside — Greyed Orange 175B with the laminae base Yellow 12B, giving the bright gold eye. Ray, bottom side — Greyed Orange 177C mostly with Greyed Red 178A at the tip and Yellow 12B at the base.

*Cone.*—Conic in shape, grows to 5 mm wide and 3 mm deep, Greyed Purple 187A.

*Disc florets.*—Corolla — 3 mm long and grows to 1 mm wide, tubular, 4 lobed, entire, acute, lobes Greyed Purple 185A and tube Yellow 11A, glabrous. Pistil — 3.5 mm long, 2-branched stigma extruding from the corolla, Orange 26B, style 3 mm long, Orange 26B, ovary 0.5 mm long, Yellow 11D. Stamen — 4, filaments 3 mm long, extruding, Greyed Purple 187A, pollen Orange 17A.

*Phyllaries.*—In 2 series, first series closet to ray florets 8 in number, ovate, entire, acuminate, in an area 5 mm deep and 6 mm wide, glabrous, Greyed Orange 174B on top half and Yellow Green 147A on bottom half; lower series 8 in number, in an area 2 mm deep and 1.5 mm wide, ovate, entire, acute, glabrous, Yellow Green 147A.

*Bloom period.*—June through September in Canby, Oreg.

*Fragrance.*—Light, daisy like.

Seed: None produced.

*Fertility.*—Infertile.

Disease and pests: *Coreopsis* are susceptible to mildew and fungal spots. None of these have been observed on plants grown under commercial conditions in Canby, Oreg.

COMPARISONS TO SIMILAR *COREOPSIS*

Compared to *Coreopsis* 'Limerock Ruby' (U.S. Plant Pat. No. 15,455), this new cultivar has smaller flowers of copper rather than rose pink and a much more compact habit.

Compared to *Coreopsis* 'Rum Punch' (U.S. Plant patent application Ser. No. 11/488,815), the new cultivar has smaller flowers of copper rather than orangey rose and a much more compact habit.

Compared to co-pending applications for *Coreopsis* 'RP #4' (U.S. Plant patent application Ser. No. 11/592,083) and 'RP #5' (U.S. Plant patent application Ser. No. 11/592,053), the new cultivar has a much more compact habit.

I claim:

1. A new and distinct *Coreopsis* plant as herein illustrated and described.

* * * * *

UNITED STATES PATENT AND TRADEMARK OFFICE

CERTIFICATE OF CORRECTION

PATENT NO. : PP 18,502 P2
APPLICATION NO. : 11/592654
DATED : February 19, 2008
INVENTOR(S) : Harini Korlipara It is certified that error appears in the above-identified patent and that said Letters Patent is hereby corrected as shown below:

On the Title Page and Col. 1:

In item (54), the title of the invention, "'RP1'" should be --'RP #1'--.

Signed and Sealed this

Twenty-ninth Day of July, 2008

JON W. DUDAS
*Director of the United States Patent and Trademark Office*